United States Patent
Boland (10) Patent No.: US 10,195,644 B2
(45) Date of Patent: Feb. 5, 2019

(54) TISSUE ENGINEERING DEVICE AND CONSTRUCTION OF VASCULARIZED DERMIS

(71) Applicant: BOARD OF REGENTS, THE UNIVERSITY OF TEXAS SYSTEM, Austin, TX (US)

(72) Inventor: Thomas Boland, El Paso, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 781 days.

(21) Appl. No.: 13/766,466

(22) Filed: Feb. 13, 2013

(65) Prior Publication Data
US 2014/0228970 A1 Aug. 14, 2014
US 2017/0087590 A9 Mar. 30, 2017

Related U.S. Application Data

(60) Provisional application No. 61/598,683, filed on Feb. 14, 2012.

(51) Int. Cl.
*B05D 5/00* (2006.01)
*A61F 2/10* (2006.01)

(52) U.S. Cl.
CPC .............. *B05D 5/00* (2013.01); *A61F 2/105* (2013.01); *A61F 2240/001* (2013.01)

(58) Field of Classification Search
None
See application file for complete search history.

(56) References Cited

U.S. PATENT DOCUMENTS

| | | |
|---|---|---|
| 2004/0115176 A1* | 6/2004 | Swartz .................. A61L 27/225 424/93.7 |
| 2004/0203146 A1 | 10/2004 | Gazit et al. |
| 2009/0035349 A1 | 2/2009 | Gazit et al. |
| 2009/0169642 A1 | 7/2009 | Fradette et al. |
| 2011/0212501 A1 | 9/2011 | Yoo |
| 2011/0250688 A1 | 10/2011 | Hasan |
| 2012/0039855 A1 | 2/2012 | Atlas et al. |
| 2012/0171257 A1 | 7/2012 | Inanc et al. |

OTHER PUBLICATIONS

Mingen Xu et al. An cell-assembly derived physiological 3D model of the metabolic syndrome, based on adipose-derived stromal cells and a gelatin/alginate/fibrinogen matrix Biomaterials 31 (2010) 3868-3877 Available online Feb. 12, 2010.*
M.W. Laschke et al Vascularisation of Porous Scaffolds Is Improved by Incorporation of Adipose Tissue-Derived Microvascular Fragments. ECM Journal V o l . 2 4, 2012 (pp. 266-277).*
Edwin C. M. Madman et al. Adipocyte extracellular matrix composition, dynamics and role in obesity Cell. Mol. Life Sci. (2010) 67: 1277-1292 Published online: Jan. 27, 2010.*
Cui, X. et al., "Human microvasculature fabrication using thermal inkjet printing technology," Biomaterials (2009) 30(31):6221-6227.
Griffith, C. K. et al. "Diffusion Limits of an In Vitro Thick Prevascularized Tissue." Tissue Engineering (2005) 11(1/2):257-266.
Mironov, V. et al., "Organ printing: computer-aided jet-based 3D tissue engineering," Trends in Biotechnology (2003) 21(4):157-161.
Papavasiliou, G. et al., "Strategies for Vascularization of Polymer Scaffolds," J. Investig. Med. (2010) 58(7).838-844.
Sun, W. et al., "Computer-aided tissue engineering: overview, scope and challenges," Biotechnol. Appl. Biochem. (2004) 39(1):29-47.
Wust, S. et al., "Controlled Positioning of Cetts in Biomaterials—Approaches Towards 3D Tissue Printing," J. Funct. Biomater. (2011) 2(3):119-154.
PCT International Search Report dated May 29, 2013 for PCT/US2013/025938.
Mironov, V. et al., "Organ printing: Tissue spheroids as building blocks," Biomaterials (2009) 30(12):2164-2174.
Supplemental European Search Report dated Nov. 3, 2015 in EP 13 74 9912.

* cited by examiner

*Primary Examiner* — Joseph Woitach
(74) *Attorney, Agent, or Firm* — Norton Rose Fulbright US LLP (57) ABSTRACT

An inkjet printing method, system, and computer-usable tangible storage device to print cells and biomaterials for three-dimensional cellular scaffolds and engineered skin grafts are disclosed. The process simultaneously deposits living cells, nutrients, growth factors, therapeutic drugs along with biomaterial scaffolds at the right time and location. This technology can also be used for the microvasculature fabrication using appropriate human microvascular endothelial cells and fibrin to form the microvasculature. When printing human microvascular endothelial cells in conjunction with the fibrin, the cells aligned themselves inside the channels and proliferated to form confluent linings. The 3D tubular structure was also found in the printed patterns. Simultaneously printing biological materials to form a three-dimensional cellular scaffold promotes human microvascular endothelial cell proliferation and microvasculature formation.

7 Claims, 10 Drawing Sheets

|  | Fibrinogen (mg/ml) | Thrombin (unit/ml) | CaCl$_2$ (mM) | Polymerization time (min) | Observation of printed fibrin scaffold |
|---|---|---|---|---|---|
| Concentration tested 1 | 30 | 20 | 40 | N/A | N/A |
| Concentration tested 2 | 60 | 50 | 40 | 10 | Broken and discontinuous |
| Concentration tested 3 | 60 | 50 | 80 | 6 | Continuous with minor deformations |
| Concentration tested 4 | 60 | 100 | 80 | 6 | Diffused |
| Concentration tested 5 | 60 | 100 | 160 | 5 | Seriously diffused |

FIG. 11

TISSUE ENGINEERING DEVICE AND CONSTRUCTION OF VASCULARIZED DERMIS

CROSS REFERENCE TO RELATED APPLICATIONS

This patent application claims the benefit under 35 U.S.C. § 119(e) of U.S. Provisional Patent Application Ser. No. 61/598,683 filed on Feb. 14, 2012 and entitled "INTRAOPERATIVE ADIPOSE TISSUE ENGINEERING DEVICE AND CONSTRUCTION OF VASCULARIZED DERMIS," which is hereby incorporated by reference in its entirety.

FIELD OF THE INVENTION

The disclosed embodiments relate to cell printing technology and tissue engineering. The disclosed embodiments further relate to a vascularized dermis produced using cell printing techniques. The disclosed embodiments also relate to an intraoperative adipose tissue engineering device.

BACKGROUND

Engineered tissues can be supported by the diffusion of nutrients from host vasculature. When the thickness of engineered tissue, however, exceeds 150-200 µm, the tissue's depth surpasses the oxygen diffusion limitation. Therefore, functional vasculatures within engineered tissues must be created to both supply cells with oxygen and nutrients and remove the waste products.

Reproduction of engineered tissue using various cell types with functional microvasculatures has not been successfully addressed. Therefore, a need exists for an improved cell printing technique utilizing inkjet printing technology to produce replacement cellular scaffolds, tissues, and organs.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide for improved cell printing technology.

It is another aspect of the disclosed embodiments to provide for a vascularized dermis produced using cell printing.

It is a further aspect of the disclosed embodiments to provide for an intraoperative adipose tissue engineering device.

The above and other aspects can be achieved as is now described. An inkjet printing method, system, and computer-usable tangible storage device to print cells and biomaterials for three-dimensional cellular scaffolds are disclosed. The process simultaneously deposits living cells, nutrients, growth factors, therapeutic drugs along with biomaterial scaffolds at the right time and location. This technology can also be used for the microvasculature fabrication using appropriate human microvascular endothelial cells and fibrin to form the microvasculature. When printing human microvascular endothelial cells in conjunction with the fibrin, the cells aligned themselves inside the channels and proliferated to form confluent linings. The 3D tubular structure was also found in the printed patterns. Simultaneously printing biological materials to form a three-dimensional cellular scaffold promotes human microvascular endothelial cell proliferation and microvasculature formation.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
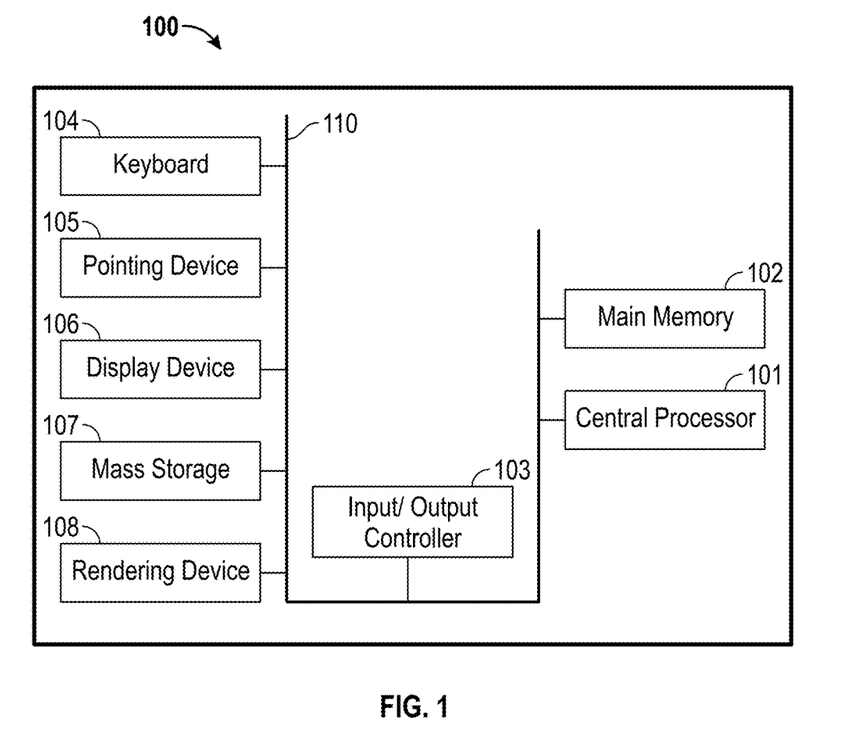
FIG. 1 illustrates a schematic view of a data-processing system in which an embodiment may be implemented, in accordance with the disclosed embodiments.
Figure 2:
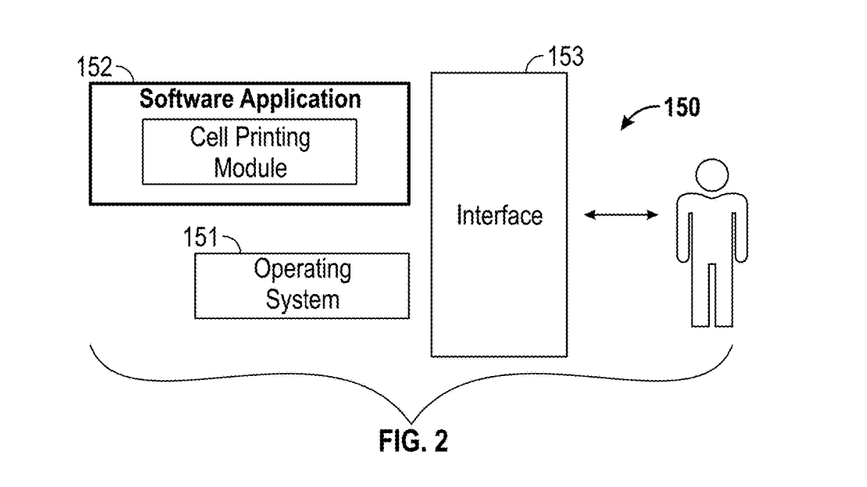
FIG. 2 illustrates a schematic view of a software system including an operating system, application software, and a user interface, in accordance with the disclosed embodiments.
Figure 3:
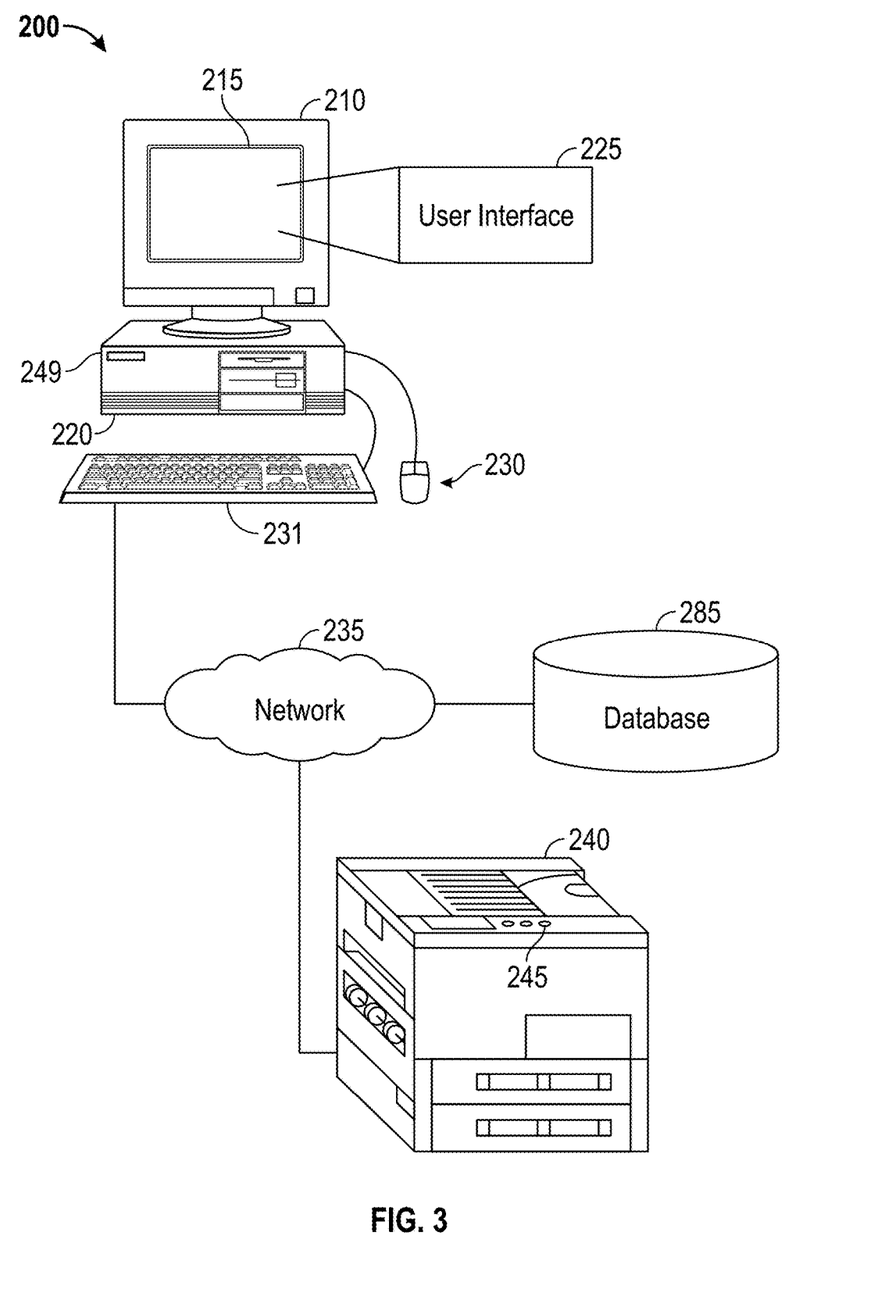
FIG. 3 illustrates a graphical representation of a network of data-processing systems, in accordance with the disclosed embodiments.

FIGS. 1-3 are provided as exemplary diagrams of data-processing environments in which embodiments of the present invention may be implemented. It should be appreciated that FIGS. 1-3 are only exemplary and are not intended to assert or imply any limitation with regard to the environments in which aspects or embodiments of the disclosed embodiments may be implemented. Many modifications to the depicted environments may be made without departing from the spirit and scope of the present invention.

FIG. 1 illustrates a schematic view of a data-processing system in which an embodiment may be implemented. As illustrated in FIG. 1, the disclosed embodiments may be implemented in the context of a data-processing system 100 comprising, for example, a central processor 101, a main memory 102, an input/output controller 103, a keyboard 104, a pointing device 105 (e.g., mouse, track ball, pen device, or the like), a display device 106, and a mass storage 107 (e.g., hard disk). Additional input/output devices, such as a rendering device 108 (e.g., printer, scanner, fax machine, etc), for example, may be associated with the data-processing system 100 as desired. As illustrated, the various components of data-processing system 100 communicate electronically through a system bus 110 or similar architecture. The system bus 110 may be a subsystem that transfers data between, for example, computer components within data-processing system 100 or to and from other data-processing devices, components, computers, etc.

FIG. 2 illustrates a computer software system 150 for directing the operation of the data-processing system 100 depicted in FIG. 1, in accordance with the disclosed embodiments. Software application cell printing module 152, stored in main memory 102 and on mass storage 107, generally includes a kernel or operating system 151 and a shell or interface 153. One or more application programs, such as software application module 152, may be "loaded" (i.e., transferred from mass storage 107 into the main memory 102) for execution by the data-processing system 100. The data-processing system 100 receives user commands and data through user interface 153; these inputs may then be acted upon by the data-processing system 100 in accordance with instructions from operating module 151 and/or software application module 152.

The following discussion is intended to provide a brief, general description of suitable computing environments in which the system and method may be implemented. Although not required, the disclosed embodiments will be described in the general context of computer-executable instructions, such as program modules, being executed by a single computer.

Generally, program modules include, but are not limited to, routines, subroutines, software applications, programs, objects, components, data structures, etc., that perform particular tasks or implement particular abstract data types and instructions. Moreover, those skilled in the art will appreciate that the disclosed method and system may be practiced with other computer system configurations such as, for example, hand-held devices, multi-processor systems, data networks, microprocessor-based or programmable consumer electronics, networked PCs, minicomputers, mainframe computers, servers, and the like.

Note that the term module as utilized herein may refer to a collection of routines and data structures that perform a particular task or implements a particular abstract data type. Modules may be composed of two parts: an interface, which lists the constants, data types, variable, and routines that can be accessed by other modules or routines; and an implementation, which is typically private (accessible only to that module) and which includes source code that actually implements the routines in the module. The term module may also simply refer to an application such as a computer program designed to assist in the performance of a specific task such as word processing, accounting, inventory management, etc. Such a module may also constitute a software application such as a "plug-in." Note that the term plug-in as utilized herein refers generally to a computer program that interacts with a host application (e.g., a Web browser) to provide a certain, usually very specific, function "on demand." The terms "plug-in" and "plug-in module" and "module" may be utilized interchangeably to refer to the same component or application.

The interface 153, which is preferably a graphical user interface (GUI), can serve to display results, whereupon a user may supply additional inputs or terminate a particular session. In some embodiments, operating system 151 and interface 153 can be implemented in the context of a "Windows®" system. It can be appreciated, of course, that other types of operating systems and interfaces may be alternatively utilized. For example, rather than a traditional "Windows®" system, other operation systems such as, for example, LINUX® may also be employed with respect to operating system 151 and interface 153. The software application module 152 can include a virtual card plug-in module for automatically storing and distributing contact information over a network. The virtual card plug-in module updates contact information with respect to a social and business networking system. Software application module 152, on the other hand, can include instructions such as the various operations described herein with respect to the various components and modules. Note that the term "virtual" as utilized herein refers generally to something that is created, simulated, and/or carried on by means of a computer or computer network or other data-processing system.

The descriptions herein are presented with respect to particular embodiments of the present invention, which may be embodied in the context of a data-processing system such as, for example, data-processing system 100, computer software system 150, and rendering device coupled to a data-processing apparatus through a network 200 illustrated with respect to FIGS. 1-3. Such embodiments, however, are not limited to any particular application or any particular computing or data-processing environment. Instead, those skilled in the art will appreciate that the disclosed system and method may be advantageously applied to a variety of system and application software. Moreover, the present invention may be embodied on a variety of different computing platforms including Mac iOS®, UNIX®, LINUX®, and the like.

FIG. 3 illustrates a pictorial illustration 200 of a rendering device coupled to a data-processing apparatus through a network, in accordance with the disclosed embodiments. FIG. 3 is provided as an exemplary diagram of data processing environments in which embodiments of the present invention can be implemented. It should be appreciated that FIG. 3 is only exemplary and is not intended to assert or imply any limitation with regard to the environments in which aspects or embodiments of the present invention can be implemented. Many modifications to the depicted environments can be made without departing from the spirit and scope of the present invention.

Referring to FIG. 3, system 200 includes a rendering device 240 that communicates with a data-processing system 210 through a network 235. The data-processing system 210 can be, for example, a personal computer or other computing device, and generally includes a central processor 220, a display device 215, a keyboard 231, and a pointing device 230 (e.g., mouse, track ball, pen device, or the like). Note that in other embodiments, the rendering device 240 may communicate directly with the data-processing system 210, rather than through a network such as, for example, network 235. The network 235 can be coupled to a database 285.

Note that as utilized herein, the term rendering device may refer to an apparatus or system such as a printer, scanner, fax machine, copy machine, etc., and/or a combination thereof. Preferably, rendering device 240 is capable of multiple rendering functions such as printing, copying, scanning, faxing, etc. In some embodiments, rendering device 240 can be implemented with a single rendering function such as printing. In other embodiments, rendering device 240 can be configured to provide multiple rendering functions, such as scanning, faxing, printing and copying.

The data-processing system 210 can communicate with the rendering device 240 through, for example, a computer network 235 or other networking configuration. Network 235 may employ any network topology, transmission medium, or network protocol. Network 235 may include connections, such as wire, wireless communication links, or fiber optic cables. The rendering device 240 includes a user interface 245, such as a panel menu. The panel menu can be employed to select features and enter other data in the rendering device 240. Such interfaces may include, for example, touch screens having touch activated keys for navigating through an option menu or the like.

A rendering device driver program can be installed on the data-processing system 210 and can reside on the host device's hard drive 250. The rendering device driver program can be activated through an application interface so that a user may generate a rendering job with the driver for processing by the rendering device 240. The data-processing system 210 also includes a GUI 225 for communicating rendering device features for processing, for example, the rendering job to a user and accepting the user's selection of available rendering device features. The user interface 225 displays information and receives data through device display and/or the keyboard/mouse combination. The interface 225, also serves to display results, whereupon the user may supply additional inputs or terminate a given session. The data-processing system 210 can be, for example, any computing device capable of being integrated within a network, such as a PDA, personal computer, cellular telephone, mobile communications device, tablet device, point-of-sale terminal, server, etc.

Note that the user interface as utilized herein generally refers to a type of environment that represents programs, files, options and so forth by means of graphically displayed icons, menus, and dialog boxes on a screen. The input device of the rendering device 240 can comprise a local user interface, such as a touch-screen display or separate keypad and display or a memory fob or the like as discussed above. Alternatively or additionally, the input device can be a wireless port that receives a wireless signal containing constraint data from a portable device. The wireless signal can be an infrared or electromagnetic signal. A system administrator may input constraint data through the local user interface by manipulating the touch screen, keypad, or communicating via wireless messages through the wireless port. The administrator's portable device that communicates wirelessly can be a personal digital assistant (PDA), or the like, as noted above.

The following description is presented with respect to embodiments of the present invention, which can be embodied in the context of a data-processing system 210 and rendering device 240 depicted in FIG. 3. The rendering device 240 can comprise an inkjet printing application using commercially available inkjet printers to print cells and biomaterials for three dimensional cellular scaffolds is disclosed. Standard HP® and Canon® desktop inkjet printers, for example, can be modified to perform cell printing. Organ printing, defined as computer-aided inkjet based tissue engineering constructs 3D structures with living biological elements. An important advantage of this process is the ability to simultaneously deposit living cells, nutrients, growth factors, therapeutic drugs along with biomaterial scaffolds at the right time and location. This technology can also be used for the microvasculature fabrication using appropriate biomaterials and cells.

Cell printing technology can be used to reproduce damaged tissue using inkjet printing, a non-contact printing technique. Inkjet printers have the ability to reproduce data on a substrate with tiny ink drops. Drop-on-demand printing refers to ejected ink drops in specific locations to create the images on the substrate. An inkjet printer has high operating frequency, high orifice density, integrated power, and interconnected electronics. In thermal inkjet printers, small air bubbles are created by heating ink. The bubbles then collapse to provide the pressure pulse to eject a very tiny drop of ink out of the nozzle. The current pulse lasts a few microseconds and raises the plate temperature as high as 300° C.

A modified Hewlett-Packard® Deskjet 500 thermal inkjet printer can be used to simultaneously deposit human microvascular endothelial cells and fibrin to form the microvasculature. It is understood that other printer models can be used in accordance with the disclosed embodiments. HP® Deskjet 500 inkjet printer has a droplet volume of 130 pL. There are 50 firing nozzles on the printer head and the actual heating occurs in a 10-μs pulse. The energy supplied during the printing process is transferred into kinetic energy and heating of the ink drop. Mathematical modeling studies indicated that the bulk drop temperature in the ink rises between 4 and 30 degrees Celsius above ambient during printing. This makes it possible to print living systems. It has been proved successful to print cell suspensions.

Successfully-engineered thick tissues must include vasculature to survive. Layer-by-layer approaches for customized fabrication of cell/scaffold constructs have shown some potential in building complex 3D structures. With the advent of cell printing, one may be able to build precise human microvasculature with suitable bio-ink. Human microvascular endothelial cells (i.e., "HMVEC") and fibrin can be utilized as bio-ink for microvasculature construction.

Figure 4:
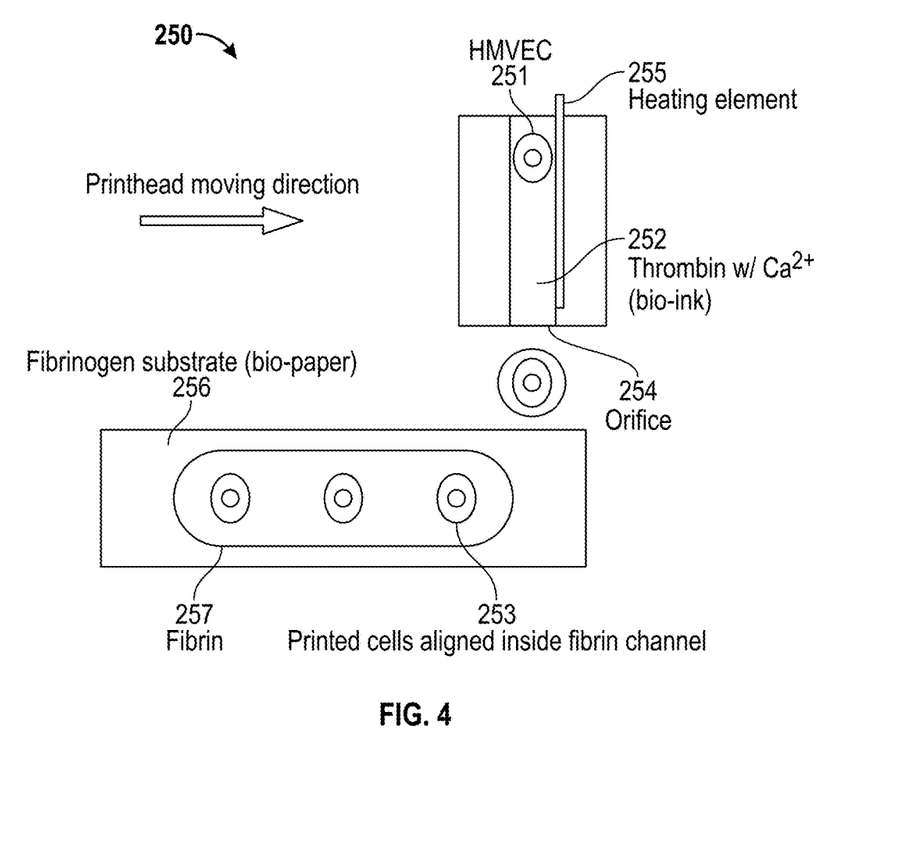
FIG. 4 illustrates a schematic illustration of simultaneous deposition of HMVEC and fibrin into a fibrin channel scaffold orifice via a modified thermal inkjet printer, in accordance with the disclosed embodiments.

FIG. 4 illustrates a schematic illustration 250 of simultaneous deposition of HMVEC 251 and fibrin 257 into a fibrin channel scaffold orifice 254 via a modified thermal inkjet printer, in accordance with the disclosed embodiments. When bio-ink 252 (e.g., thrombin with $Ca^{2+}$) is printed into a fibrinogen substrate 256 with an associated heating element 255 to form a fibrin channel 253, the cells in the bio-ink 252 are deposited into the scaffold simultaneously with a fibrin channel fabrication. The printed cells are aligned inside the fibrin channel 253, thereafter ready for cell proliferation.

For example, fibrin 257 is utilized in tissue engineering to engineer tissues with skeletal muscle cells, smooth muscle cells, and chondrocytes. Fibrin 257 plays a significant role in natural wound healing to promote cell migration, proliferation, and matrix synthesis through the incorporation of the transforming growth factor β and platelet-derived growth factors. Fibrin 257 can be produced from the patients' own blood and used as an autologous scaffold for tissue engineering. Polymerized at room temperature using fibrinogen and thrombin 252 solutions, fibrin gel has been widely used as sealant and adhesive during surgery, while fibrin glue is used as skin graft and tissue-engineered skin replacement.

Micron-sized fibrin channels can be fabricated using a drop-on-demand polymerization. This printing technique uses aqueous processes that have been shown to induce little, if any, damage to cells. When printing HMVEC 251 in conjunction with the fibrin 257, the cells aligned themselves inside the channels and proliferated to form confluent linings. The three dimensional tubular structure was also found in the printed patterns. A combined simultaneous cell and scaffold printing can promote HMVEC 251 proliferation and microvasculature formation.

Materials

MCDB 131 medium, fetal bovine serum, penicillin and streptomycin, sodium bicarbonate, L-glutamine, hydrocortisone, human recombinant epidermal growth factor, heparin, Dulbecco's phosphate buffered saline solution (DPBS), trypsin-EDTA, fibrinogen from bovine plasma, thrombin from bovine plasma were from Sigma Chemicals® (St. Louis, Mo., USA). Live/Dead Viability/Cytotoxicity Kit for mammalian cells was from Invitrogen® (Carlsbad, Calif., USA), IEC Centra-8R centrifuge was from International Equipment Company® (Needham, Mass., USA). Microprocessor controlled 280 series water bath was from Precision Scientific® (Winchester, Va., USA). Glass microscope cover slips and 35 mm tissue culture Petri dishes were from Fisher Scientific (Pittsburgh, Pa., USA). HP® DeskJet 500 inkjet printer and HP 51626A black ink cartridges were from Hewlett-Packard® (Palo Alto, Calif., USA). Advanced Micro Osmometer (Model 3300) was from Advanced Instruments, Inc.® (Norwood, Mass., USA). Zeiss Axiovert S100 UV microscope and Zeiss LSM 510 laser scanning microscope were from Carl Zeiss® (Minneapolis, Minn., USA). Electromechanical testing system was from MTS System Corporation® (Eden Prairie, Minn., USA). Hummer 6.2 sputter coater was from Anatech Ltd.® (Hayward, Calif., USA). Hitachi® S4700N field emission scanning electron microscope was from Hitachi® (Tokyo, Japan).

Thrombin and Fibrinogen Solution Preparation

Figure 5:
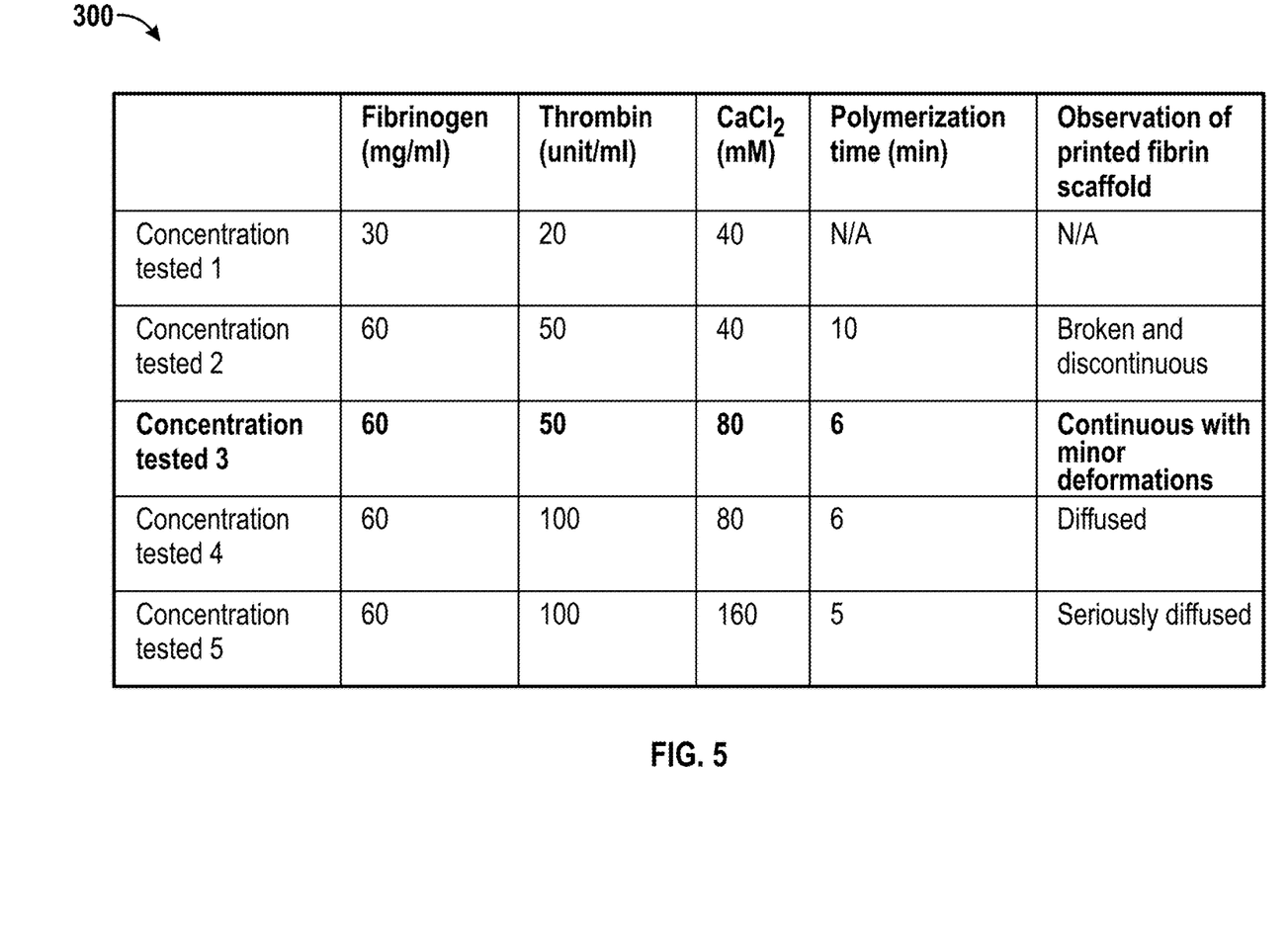
FIG. 5 illustrates a table of selected fibronigen and thrombin concentration tests for fibrin polymerization via printing, in accordance with the disclosed embodiments.

To assure prompt and optimum polymerization of fibrin gel after printing, fibrin gel polymerizations were conducted with various combinations of fibrinogen, thrombin, and $Ca^{2+}$ concentrations (as illustrated in FIG. 5). The appropriate concentrations of thrombin and fibrinogen solutions for optimum polymerization result were prepared. The thrombin solution was made using 50 unit/ml thrombin and 80 mM $Ca^{2+}$ in 1×DPBS. The concentration of fibrinogen is 60 mg/ml in distilled water. Both solutions were filter sterilized.

FIG. 5 illustrates a table 300 of selected fibronigen and thrombin concentration tests for fibrin polymerization via printing, in accordance with the disclosed embodiments. The best polymerization result via printing occurred with 60 mg/ml fibronigen, 50 unit/ml thrombin, and 80 mM $CaCl_2$. Minimum deformations and diffusions of printed fibrin pattern were observed at these concentrations.

Osmolality Study

To assure the minimum deformation (swelling) of the printed fibrin gel in the culture media, matched osmolality is required for endothelial cells culture media (MCDB 131), thrombin solution, and fibrinogen solution. Serum free MCDB 131 media, 1×DPBS, and distilled water were used to make thrombin and fibrinogen solutions for osmolality study. The osmolality of different solutions was tested using an Advanced Micro osmometer.

Endotheal cells, for example, form the inner lining of the whole cardiovascular system and have a remarkable capacity to adjust their number and arrangement to suit local requirements. Almost all tissues depend on a blood supply and a blood supply depends on endothelial cells. Endothelial cells are the only cells to form capillaries, creating an adaptable life-support system spreading into almost every region of the body. Endothelial cells extending and remodeling the network of blood vessels make it possible for tissue growth and repair (angiogenesis).

Fabrication of Fibrin Channels

HP® Deskjet 500 printer and HP® 51626A cartridges were modified to print/fabricate fibrin channels. The modified inkjet printer was UV sterilized overnight and modified ink cartridges were sprayed using 100% ethanol before using. Thrombin solution was served as bio-ink and fibrinogen was substrate on a microscope cover slip (bio-paper). After printing, the printed samples were incubated at 37° C. for 5-10 min until white printed scaffolds were observed.

Mechanical Properties of Printed Fibrin Fibers

Mechanical properties of the printed fibrin fibers were tested by stretching the sample at a constant deformation rate of 5 mm/min at room temperature. The fibers were gripped on an MTS electromechanical testing system for uni-axial tensile testing. The original data were achieved and analyzed using the software coming with the MTS system (TestWorks®, MTS System Corporation®). The elastic modulus and ultimate tensile strength (UTS) were from the acquired stress-strain data. The elastic modulus is defined as the slope of the linear part of the stress-strain curve and the highest stress which caused the fiber to break is defined as UTS.

Cell Culture and Bio-Ink Preparation

HMVEC 251 was cultured in MCDB 131 media supplemented with FBS, L-glutamine, hydrocortisone, HEGF, and heparin. The culture condition was standard at 37° C. with 5% $CO_2$ for 10 days before passaging. Culture media was changed every two days. During passaging, cell suspension was centrifuged at 1000 rpm for 5 min. The supernatant was aspirated and the cell pellet was re-suspended using 1 ml 1×DPBS. The bio-ink was made by mixing the same volume of cell suspension and 100 unit/ml thrombin with 160 mM $Ca^{2+}$ in 1×DPBS. The final condition of bio-ink has 1-8 million cells/ml HMVEC, 50 unit/ml thrombin, and 80 mM $Ca^{2+}$ in 1×DPBS.

Fabrication of Microvasculature

The biological ink mentioned above was added into a sterile modified HP® 51626A cartridge. 60 mg/ml fibrinogen solution was served as bio-paper on a microscope cover slip. UV sterilized modified HP® Deskjet 500 printer was used to print patterns. Cells in bio-ink were simultaneously deposited and aligned into the channel during the fibrin channel formation (as illustrated in FIG. 4). The printed patterns were incubated for 15-20 min at 37° C. for the printed cell attachment as well as fibrin polymerization. After that, a few drops of MCDB 131 media were carefully added onto the printed patterns for nutrition and moisture. The patterns were then cultured at 37° C. with 5% $CO_2$ for up to 21 days. Media was changed every two days during the culture.

Fluorescent Staining and Imaging of Printed Microvasculature

Live/Dead Viability/Cytotoxicity Kit was used to stain the printed HMVEC 251 in fibrin scaffolds. Printed samples were analyzed after 24 hours, 7 days, 14 days, and 21 days of printing to show the progress of the cell proliferation in the fabricated microvasculature. The staining solution was made by adding 5 μl 4 mM calcein AM and 20 μl 2 mM ethidium homodimer-1 into 10 ml 1×DPBS solution. The samples were incubated in the staining solution for 30-45 min at room temperature in the dark. Zeiss® Axiovert S100 UV microscope and Zeiss® LSM 510 confocal microscope were used to observe the 2D and 3D fluorescent images. Series fluorescent images at z-axis with frame size of 512×512 were taken using Zeiss® LSM 510 confocal microscope at the interval of 5 μm. These series confocal images were then rendered into 3D images using Imaged software to show the possible channel structure.

Integrity of Printed Microvasculature

In order to study the integrity of printed microvasculature, 10 μg/ml Texas Red conjugated dextran molecules of 3000 MW was applied to the printed microvasculature cultured for 14 and 21 days. The samples were incubated at 37° C. for 40 min in the dark before observed by LSM 510 confocal microscopy.

Results and Discussion

Osmolality of Thrombin and Fibrinogen Solution

Printed fibrin scaffold with minimum thrombin diffusion and scaffold deformations were obtained using the concentrations of 50 unit/ml thrombin, 80 mM $CaCl_2$, and 60 mg/ml fibrinogen (as illustrated in FIG. 5). Osmolality of thrombin solution of 50 unit/ml thrombin and 80 mM $Ca^{2+}$ in 1×DPBS was 359 mOsm. Osmolality of 60 mg/ml fibrinogen in distilled water was 341 mOsm. The osmolality of MCDB 131 culture media was 348 mOsm. The osmolalities of these solutions were similar. After fibrin scaffold was printed, only minor deformations of the scaffold structure in the HMVEC 251 culture media were noticed.

Printed Fibrin Scaffolds

Figure 6:
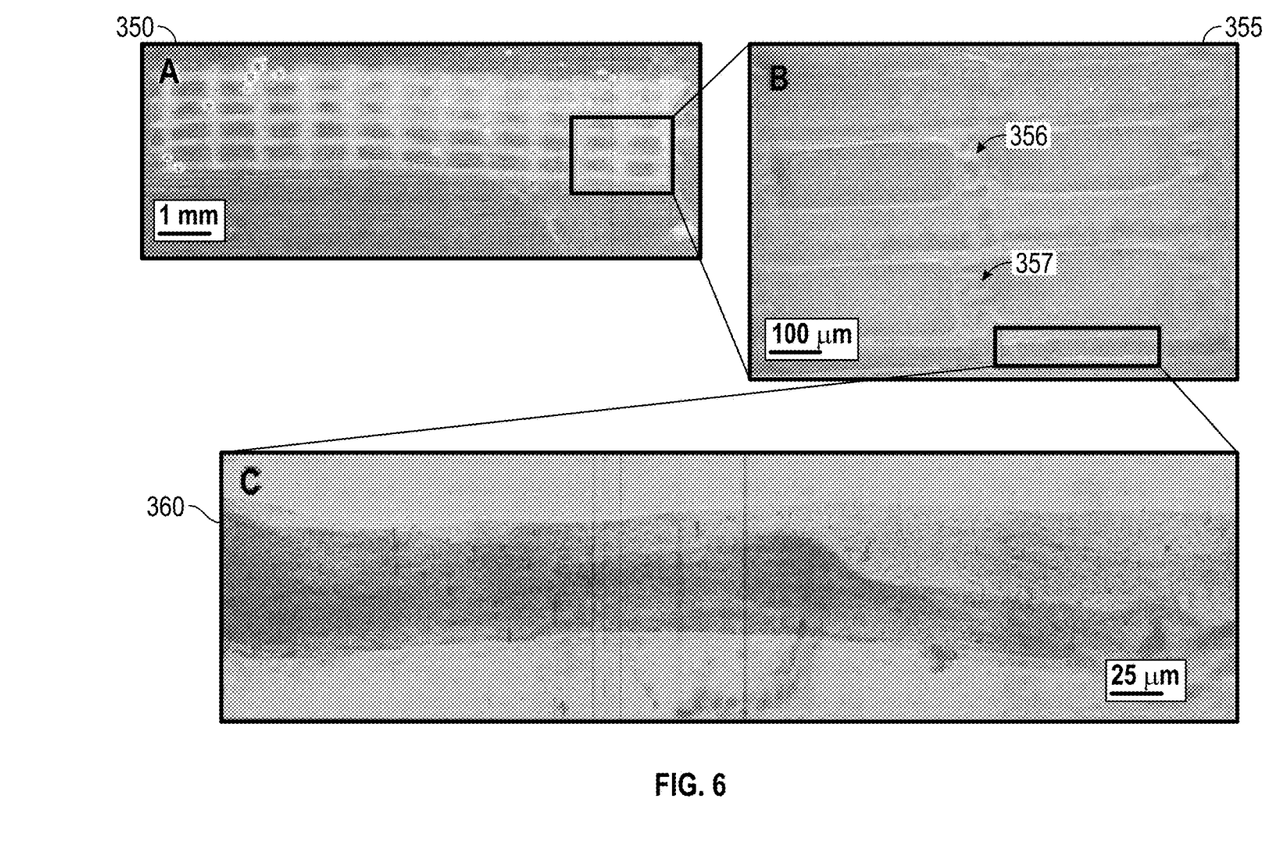
FIG. 6 illustrates pictorial illustrations of printed fibrin scaffold using a modified thermal inkjet printer, in accordance with the disclosed embodiments.

FIG. 6 illustrates pictorial illustrations 350, 355, 360 of printed fibrin scaffold using a modified HP® Deskjet 500 thermal inkjet printer, in accordance with the disclosed embodiments. The grid structure in illustration 350 illustrates the grid structure at a 1 mm magnification. The grid structure in illustration 355 illustrates the grid structure at a 100 μm magnification. The grid structure in illustration 360 illustrates the grid structure at a 25 μm magnification. The structural integrity of the printed fibrin scaffold remains sound after the print. Only minor deformations were noticed at the y-axis; the arrows 356, 357 in illustration 355 indicate these minor deformations. The higher magnified images in 355 and 360 show that the fibrin fiber structures were well aligned and straight, appropriate for cell seeding and microvasculature fabrication.

Mechanical Properties of Printed Fibrin Fibers

Using the MTS electromechanical testing system and the system software (TestWorks), the elastic modulus is 2.9±0.8 MPa and the UTS to be 1.7±0.5 MPa (n=4). The average diameter of the tested fibrin fibers was 93 μm (n=4). Using methods mentioned to estimate the upper limit of burst pressure, we estimated the burst pressure of the printed fibrin fiber to be 2955 mm Hg. Compared with the average burst pressure of tissue-engineered blood vessels which is 3340 mm Hg, and the extruded fibrin fibers with 55-65 μm diameters of UTS of 4.5 MPa by Cornwell and Pins, the mechanical properties of the printed fibrin fibers are sound.

SEM Characterization of Printed Fibrin Scaffold

Figure 7:
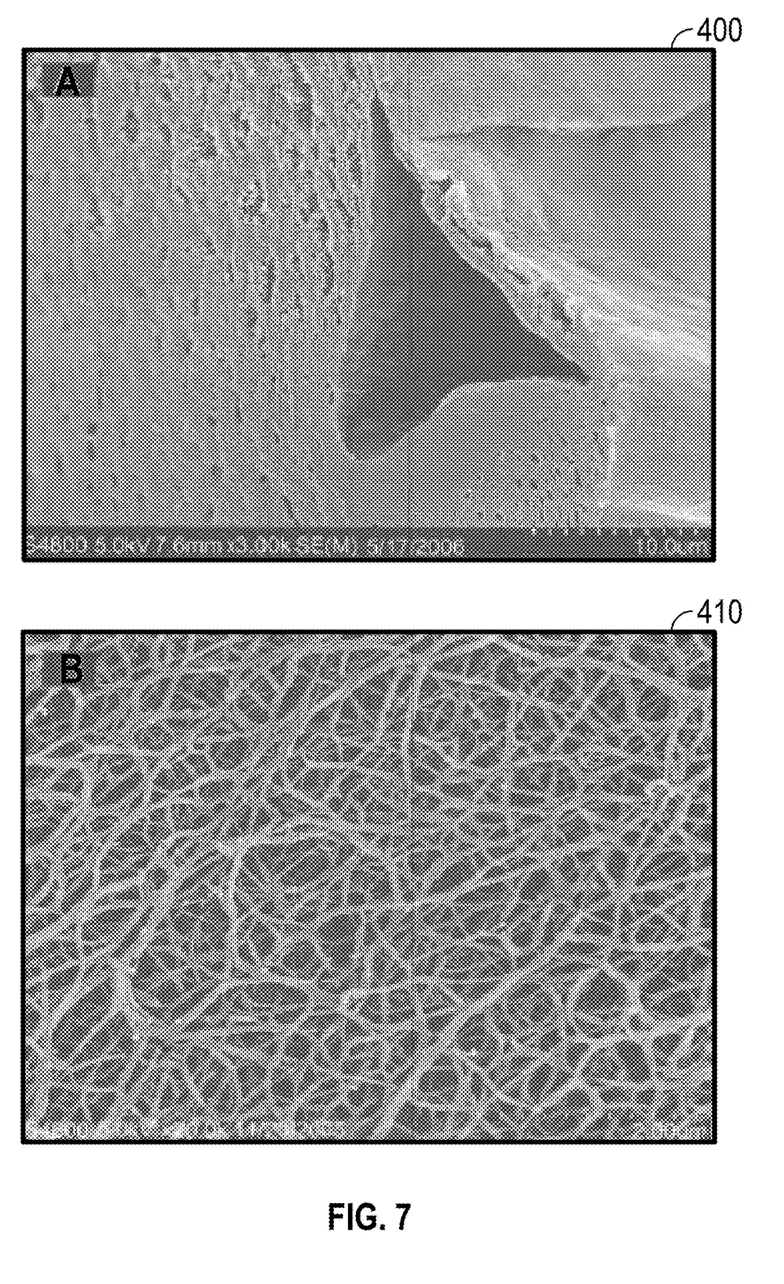
FIG. 7 illustrates pictorial illustrations of scanning electron microscope images of printed fibrin fiber, in accordance with the disclosed embodiments.

FIG. 7 illustrates pictorial illustrations 400, 410 of scanning electron microscope images of printed fibrin fiber, in accordance with the disclosed embodiments. The microstructure of printed fibrin fibers was examined using a scanning electron microscope. In illustration 400, the printed fibrin fibers were first dried in 100% ethanol at 4° C. overnight then were critically dried under vacuum and $CO_2$. After that, the dried fibers were cut through the middle to observe the possible channel structure on the cross section surface. The hole shows the channel opening of the printed hollow fibrin fiber for cell seeding and proliferation. The fixed fibers were sputter-coated with a thin layer of Chromium using the Hummer 6.2 sputter coater in 100 m Torr vacuum argon environment for a 5 min period and 10 mA of current. SEM images were taken using the Hitachi® SEM mentioned above at a 5 kV accelerating voltage. Nano-sized fibers on the printed fibrin scaffold surface which can help the cells to attached and proliferate, as illustrated in 410.

Microvasculature Fabrication of Fibrin and HMVEC

Figure 8:
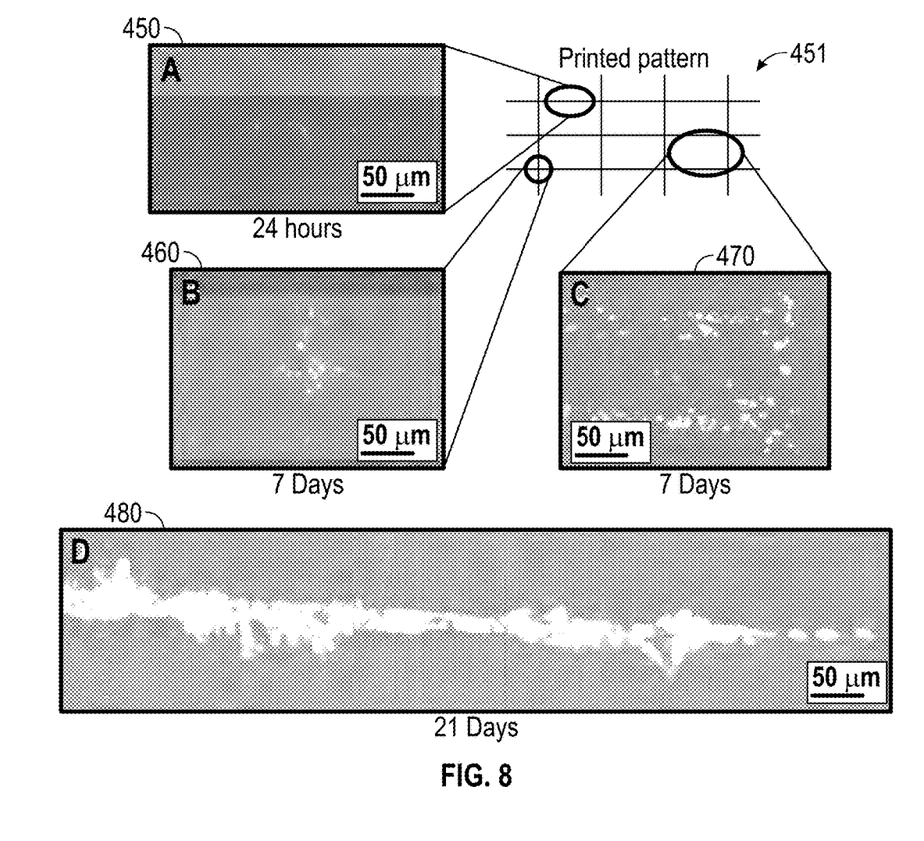
FIG. 8 illustrates pictorial illustrations of magnified, printed human microvasculature from a printed pattern, in accordance with the disclosed embodiments.

FIG. 8 illustrates pictorial illustrations 450, 460, 470, 480 of magnified, printed human microvasculature from a printed pattern 451, in accordance with the disclosed embodiments. Images 450, 460, 470, 480 are taken from different parts of the printed pattern 451 which showed the progress of printed HMVEC 251 proliferation. Illustration 450 illustrates that the printed cells aligned well after 24 hours and were ready to proliferate. This also shows the ability of the modified thermal inkjet printers to deposit the cells accurately with digital control. After 7 days, printed HMVEC 251 started to proliferate following the printed pattern 451 which is shown in 460 and 470. The deposited cells were also trying to contact and connect each other. When cultured for 21 days, 480 illustrates the printed cells aligned themselves in the fibrin channel and also proliferated to form a confluent lining. At the right end of the printed microvasculature, the proliferated cells were trying to reach the other deposited cells and connect with them. This shows the potential of using the modified thermal inkjet printers to simultaneously deposit fibrin and HMVEC 251 for human microvasculature fabrication.

Channel Structure of Printed Human Microvasculature

Figure 9:
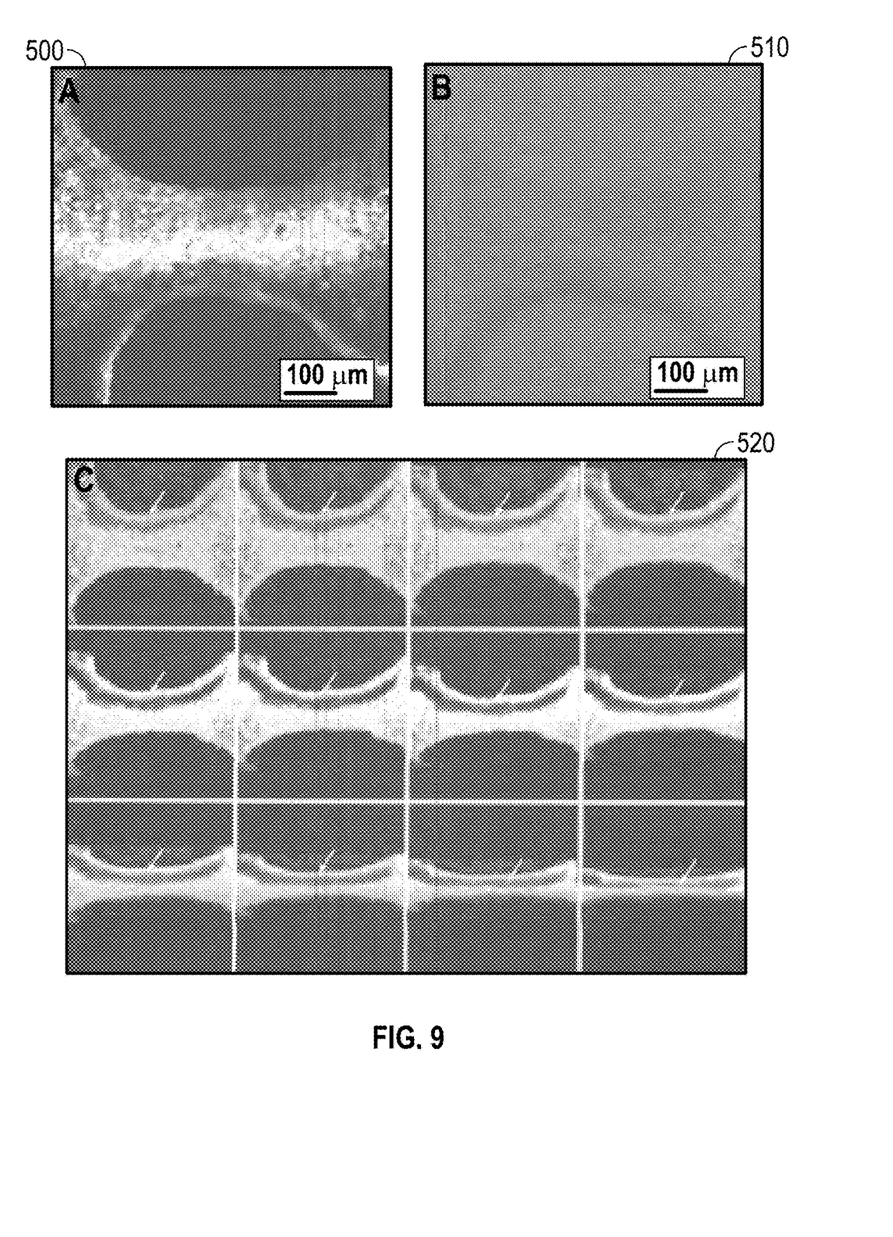
FIG. 9 illustrates pictorial illustrations of the channel structure of cultured and printed microvasculature, in accordance with the disclosed embodiments.

FIG. 9 illustrates pictorial illustrations 500, 510, 520 of the channel structure of printed microvasculature cultured for 21 days, in accordance with the disclosed embodiments. Pictorial illustrations 500, 510, and 520 illustrate the tubular structure of the printed human microvasculature cultured for 21 days. Illustration 500 shows the cells aligned inside the fibrin channel. Fluorescent stained printed cells aligned inside the fibrin scaffold. Illustration 510 is a DIC image of the printed fibrin fiber. Illustration 520 is a confocal series image at the z-axis and was taken at 5 μm intervals of the printed structure. These series images at the z-axis were rendered into a 3D image using ImageJ to show the channel structure. The rendered 3D image was turned around along x-axis to show the 3D structure of the printed structure. Twelve consequent images were taken from the 3D movie as shown in illustration 520. During proliferation, the endothelial cells tended to form channel or tubular structure as a functionality of angiogenesis. The edge of the channel structure is clearly indicated by white arrows in illustration 520. The proliferated endothelial cells were functional and attempting to seal inside of the fibrin channel and form a tubular structure. It also shows that simultaneous deposition of endothelial cells and fibrin gel using thermal inkjet printing technology can be used for human microvasculature fabrication.

Integrity of Printed Human Microvasculature

Figure 10:
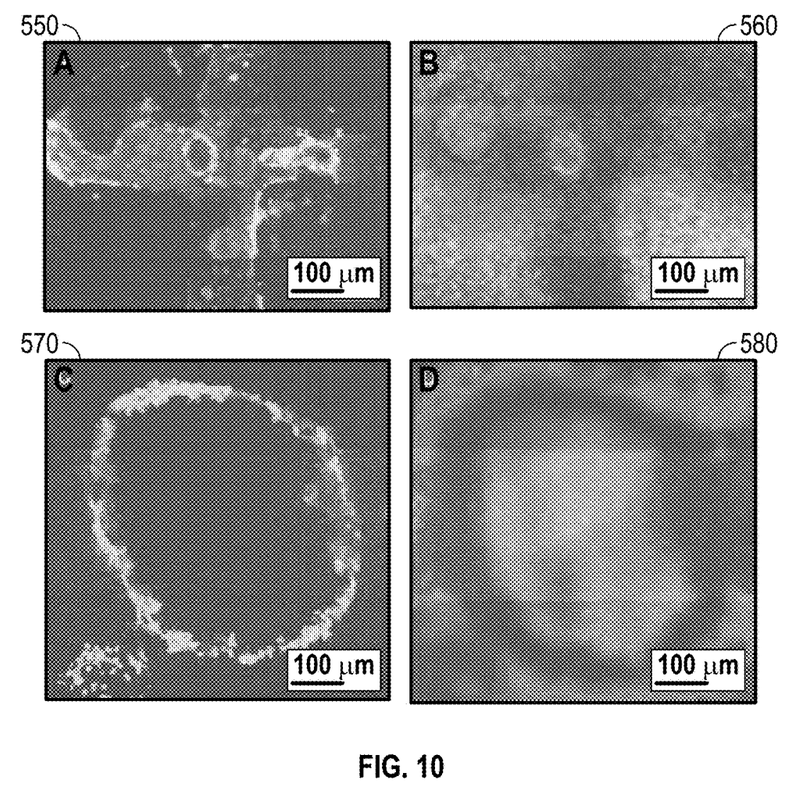
FIG. 10 illustrates pictorial illustrations of the integrity of the printed human microvasculature, in accordance with the disclosed embodiments.

FIG. 10 illustrates pictorial illustrations of the integrity of the printed human microvasculature, in accordance with the disclosed embodiments. Illustration 550 illustrates a printed perpendicular microvasculature cultured for 14 days. The printed perpendicular microvasculature was cultured for 14 days. Defects were found in the structure indicating the cells required more time to proliferate into confluence. Illustration 560 illustrates the integrity of the printed structure stained using Texas Red conjugated dextran molecules with 3000 MW. Some integrity was demonstrated by the expulsion of red fluorescent dextran molecules from the printed structure. Illustration 570 illustrates a printed ring shaped microvasculature cultured for 21 days. Illustration 580 illustrates the integrity of the printed structure using the same dextran molecules.

It is not required that the printed human microvasculature be leak-proof. Moderate integrity, however, is required for this fabricated structure. Texas Red conjugated dextran molecules with 3000 MW have an approximate size of 28 Å. Cells in a printed microvasculature cultured for 14 days were not confluent yet and some defects were observed in the printed structure (as illustrated in 550). However, the structure already had some integrity by expelling the red fluorescent dextran molecules from the structure (as illustrated in 560). Printed ring structure cultured for 21 days had much better integrity (as illustrated in 570). Almost all the dextran molecules were excluded from the structure as shown by the significant red fluorescent difference between the inside and the outside of the microvasculature (as illustrated in 580).

From the printing study of the fibrin gel and HMVEC 251 for microvasculature fabrication, human microvascular endothelial cells can be simultaneously deposited along with the appropriate biomaterials (i.e., fibrin) for microvasculature fabrication using the modified thermal inkjet printers. The printed endothelial cells proliferate to form a confluent lining along with the fibrin scaffold after 21 days of culture. The rendered 3D channel structure through the series confocal images at the z-axis shows the functionality of the printed human microvasculature. Printed endothelial cells proliferate to form a tubular structure and seal inside the fibrin channel. The fabricated microvasculature also shows some integrity after being cultured for 14 days. Much better integrity is observed from the printed structure cultured for 21 days.

Figure 11:
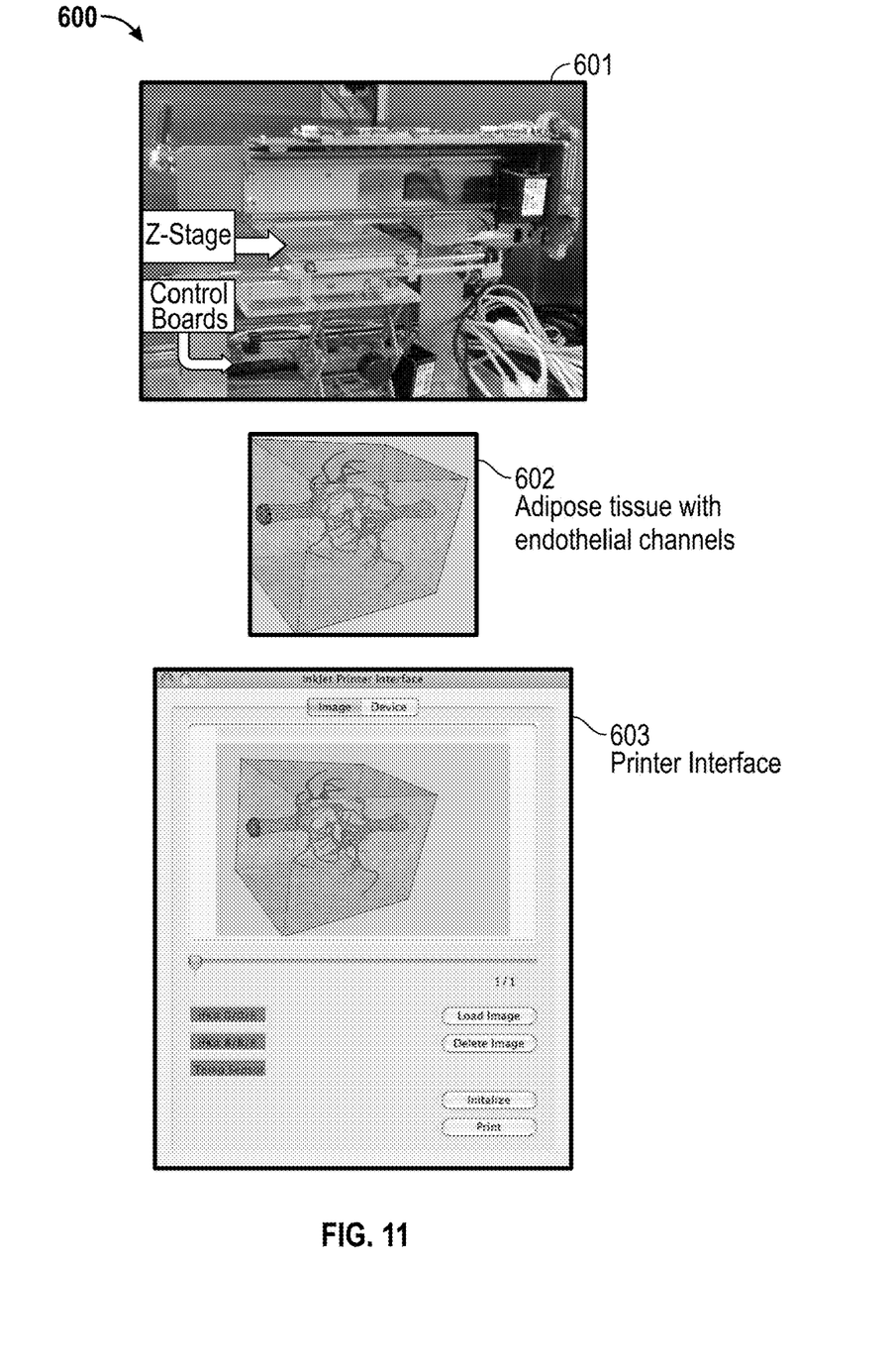
FIG. 11 illustrates a pictorial illustration of an intraoperative adipose tissue engineering device, in accordance with the disclosed embodiments.

FIG. 11 illustrates a pictorial illustration 600 of an intra-operative adipose tissue engineering device 601, in accordance with the disclosed embodiments. The device 601 can be used to fabricate adipose tissue constructs 602 from cells that were freshly obtained during lipoplasty and print viable cells in three dimensions. The printer interface 603, which is preferably a graphical user interface (GUI), can serve to display cell printing options, cell printing results, whereupon a user may supply additional inputs or terminate a particular session.

The device 601 is capable of generating hollow fibrin tubes that are lined with endothelial cells, surrounded by a matrix of other adipose-derived cells. Adipose tissue has not been engineered with endothelial-lined vessels. The device can layer these tubes arbitrarily in three dimensions within the cell/fibrinogen/collagen matrix. A precise three-dimensional reconstruction of adipose-like tissue with endothelial cell tubes can then be formed. The tissue can be used in tissue augmentation from cancer resections or to fill other defects where adipose tissue is desired. The device 601 uses image-based control of the size and thickness of the reconstructed tissue and can thus be interfaced with most three dimensional image modeling software. Processing and adipose reconstruction will be done intraoperatively with the device never leaving the surgical room, for example.

By pre-fabricating vascular channels into a tissue construct, the integration with existing tissue may be quicker, thus the survival rate may be improved. If low survival rates from partial necrosis can be overcome, the method of soft tissue augmentation can be performed without detectable scarring on the donor or recipient site and without complications associated with foreign materials. Thus, if the clinical efficacy and safety of the procedure can be improved, the disclosed embodiments are a strong cosmetic and reconstructive tool for soft tissue augmentation.

The disclosed embodiments can include, for example: vascularized mesh to support growth of multiple types of cells; vasculature comprising at least one of or a combination of cells (e.g., fibroblasts, keratinocytes, melanocytes, etc.); vascularization with adipose; cells can originate from allogeneic or autologous sources; printing a bi-layer (i.e., multilayer) skin construct, with the layers having different densities of cell types such as, for example, a dermal layer and an epidermal layer; building an "exact" size match (i.e., all three dimensions) wound dressing or tissue replacement construct based on a "photo" or other image such as MRI or scan; utilizing software and printing to produce the matched wound dressing or tissue replacement construct; and temperature control of the printer stage and cartridge.

Embodiments include, for example, the treatment of lipoaspirates to separate CD-31 positive endothelial-like cells form a mixture of adipose cells, adipose tissue-derived stem cells, and other adipose tissue-derived cells, such as interstitial fibroblasts. The endothelial-like cells can be mixed with buffer and thrombin and added to the device. The remaining cells can be mixed with buffer, fibrinogen, and collagen.

Based on the foregoing, it can be appreciated that a number of different embodiments, preferred and alternative are disclosed herein. For example, in one embodiment, a computer-implemented method for rendering a microvasculature is disclosed. The method can include steps for: rendering biological ink via a rendering device; rendering a material along with the biological ink via the rendering device; and aligning the rendered biological ink and the rendered material into fibrin channels wherein the biological ink proliferates in a presence of the rendered material to form the microvasculature.

In an embodiment, the biological ink comprises human microvascular endothelial cells and fibrin and the material comprises at least one of living cells, a nutrient, a growth factors, a therapeutic drug. The rendering device comprises an ink jet printer, wherein a printer cartridge of the ink jet printer is modified to accommodate the biological ink and the material. In another embodiment, rendering the material along with the biological ink via the rendering device can further include a step for simultaneously depositing at least one of living cells, a nutrient, a growth factor, and a therapeutic drug along with the human microvascular endothelial cells and fibrin via the rendering device. In other embodiments, the aligning the human microvascular endothelial cells and the fibrin inside fibrin channels further includes a step for utilizing drop-on-demand polymerization wherein the human microvascular endothelial cells and fibrin proliferate, and wherein the microvasculature is functional and comprises a confluent lining and a three-dimensional cellular scaffold.

In another embodiment, the method includes a step for heating the human microvascular endothelial cells, the fibrin, and the material to a preferable temperature between four degrees Celsius and thirty degrees Celsius above ambient temperature during rendering, wherein energy supplied during the rendering is transferred into kinetic energy to heat the human microvascular endothelial cells, the fibrin, and the material. In other embodiments, the method includes steps for: supporting growth of multiple types of cells via a vasculature, the vasculature comprising at least one fibroblasts, interstitial fibroblasts, keratinocytes, melanocytes, adipose cells, adipose tissue-derived stem cells, cells from allogeneic or autologous sources; rendering a multiple-layer tissue construct, wherein the multiple-layer tissue construct comprises a plurality of densities and cell types, and wherein the multiple-layer tissue construct comprises at least one of a skin construct, an adipose construct, and a combination skin construct and adipose construct; and rendering at least one of a size match wound dressing, tissue replacement construct, and skin graft.

In other embodiments, a system for rendering a microvasculature is disclosed. The system can include a processor, a data bus coupled to the processor; and a computer-usable tangible storage device storing computer program code, the computer program code comprising program instructions executable by the processor for rendering a microvasculature. The program instructions can include: program instructions to render biological ink via a rendering device; program instructions to render a material along with the biological ink via the rendering device; and program instructions to align the rendered biological ink and the rendered material into fibrin channels wherein the biological ink proliferates in a presence of the rendered material to form the microvasculature.

In other embodiments, the biological ink comprises human microvascular endothelial cells and fibrin. The rendering device comprises an ink jet printer, wherein a printer cartridge of the ink jet printer is modified to accommodate the biological ink and the material. The material comprises at least one of living cells, a nutrient, a growth factors, a therapeutic drug. In another embodiment, the program instruction to render the material along with the biological ink via the rendering device further comprises program instructions to simultaneously deposit at least one of living cells, a nutrient, a growth factor, and a therapeutic drug along with the human microvascular endothelial cells and fibrin via the rendering device. In an embodiment, the program instruction to align the human microvascular endothelial cells and the fibrin inside fibrin channels further comprises program instructions to utilize drop-on-demand polymerization wherein the human microvascular endothelial cells and fibrin proliferate, and wherein the microvasculature is functional and comprises a confluent lining and a three-dimensional cellular scaffold.

In another embodiment, the system includes program instructions to heat the human microvascular endothelial cells, the fibrin, and the material to a preferable temperature between four degrees Celsius and thirty degrees Celsius above ambient temperature during rendering, wherein energy supplied during the rendering is transferred into kinetic energy to heat the human microvascular endothelial cells, the fibrin, and the material. In other embodiments, the system includes: program instructions to support growth of multiple types of cells via a vasculature, the vasculature comprising at least one fibroblasts, interstitial fibroblasts, keratinocytes, melanocytes, adipose cells, adipose tissue-derived stem cells, cells from allogeneic or autologous sources; program instructions to render a multiple-layer tissue construct, wherein the multiple-layer tissue construct comprises a plurality of densities and cell types, and wherein the multiple-layer tissue construct comprises at least one of a skin construct, an adipose construct, and a combination skin construct and adipose construct; and program instructions to render at least one of a size match wound dressing, tissue replacement construct, and skin graft.

In yet another embodiment, a computer-usable tangible storage device storing computer program code for rendering a microvasculature is disclosed. The computer program code comprising program instructions executable by a processor, includes computer program instructions for: program instructions to render biological ink via a rendering device; program instructions to render a material along with the biological ink via the rendering device; and program instructions to align the rendered biological ink and the rendered material into fibrin channels wherein the biological ink proliferates in a presence of the rendered material to form the microvasculature.

In an embodiment, the program instruction to render said material along with the biological ink via the rendering device further comprises program instructions to simultaneously deposit at least one of living cells, a nutrient, a growth factor, and a therapeutic drug along with human microvascular endothelial cells and fibrin via the rendering device. The program instructions further include program instructions to align the human microvascular endothelial cells and the fibrin inside fibrin channels further comprises program instructions to utilize drop-on-demand polymerization wherein the human microvascular endothelial cells and fibrin proliferate, and wherein the microvasculature is functional and comprises a confluent lining and a three-dimensional cellular scaffold.

In another embodiment, program instructions further include program instructions to heat the human microvascular endothelial cells, the fibrin, and the material to a preferable temperature between four degrees Celsius and thirty degrees Celsius above ambient temperature during rendering, wherein energy supplied during the rendering is transferred into kinetic energy to heat the human microvascular endothelial cells, the fibrin, and the material. In yet other embodiments, the program instructions include: program instructions to support growth of multiple types of cells via a vasculature, the vasculature comprising at least one fibroblasts, interstitial fibroblasts, keratinocytes, melanocytes, adipose cells, adipose tissue-derived stem cells, cells from allogeneic or autologous sources; program instructions to render a multiple-layer tissue construct, wherein the multiple-layer tissue construct comprises a plurality of densities and cell types, and wherein the multiple-layer tissue construct comprises at least one of a skin construct, an adipose construct, and a combination skin construct and adipose construct; and program instructions to render at least one of a size match wound dressing, tissue replacement construct, and skin graft.

In an embodiment, an engineered adipose tissue graft is disclosed. The graft comprises: a plurality of cells and biomaterials in an engineered fibrin scaffold; tube-like channels within the cellular scaffold; and a plurality of microvascular channels within the fibrin for vascularization of the engineered adipose tissue graft. In another embodiment, the plurality of cells comprises at least one of fibroblasts, interstitial fibroblasts, keratinocytes, melanocytes, adipose cells, adipose tissue-derived stem cells, cells from an allogenic source, and cells from a autologous source. In other embodiments, the biomaterials comprise at least one of living cells, a nutrient, a growth factor, a therapeutic drug. In another embodiment, the vasculature comprises at least one of fibroblasts, interstitial fibroblasts, keratinocytes, melanocytes, adipose cells, adipose tissue-derived stem cells, cells from an allogenic source, and cells from a autologous source. In another embodiment, the plurality of microvascular channels are interconnected and of dimensions less than 200 micrometers in diameter.

It will be appreciated that variations of the above-disclosed and other features and functions, or alternatives thereof, may be desirably combined into many other different systems or applications. Furthermore, various presently unforeseen or unanticipated alternatives, modifications, variations or improvements therein may be subsequently made by those skilled in the art which are also intended to be encompassed by the following claims.

What is claimed is:

1. An adipose tissue graft, comprising:
    a plurality of fibrin channels having endothelial cells aligned inside the fibrin channel, the fibrin channel being surrounded by a matrix comprising adipose cells, fibrinogen, and collagen.

2. The adipose tissue graft of claim 1, further comprising fibroblasts, interstitial fibroblasts, or adipose tissue-derived stem cells.

3. The adipose tissue graft of claim 1, further comprising one or more of a nutrient, a growth factor, or a therapeutic drug.

4. The adipose tissue graft of claim 1, further comprising cells from an autologous or allogenic source.

5. The adipose tissue graft of claim 1, wherein the endothelial cells are from a lipoaspirate.

6. The adipose tissue graft of claim 5, wherein the endothelial cells are CD-31 positive endothelial-like cells.

7. The adipose tissue graft of claim 1, wherein the channels are interconnected and arranged in a grid-like pattern.

* * * * *